Figure 1:
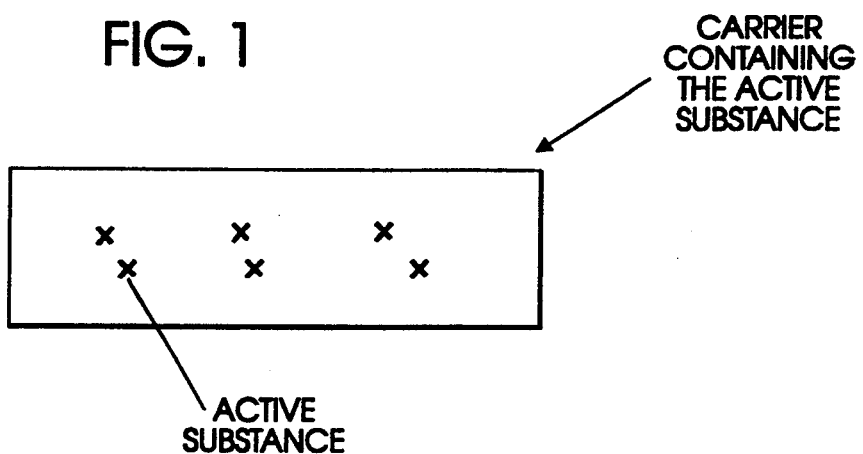

United States Patent [19]

Itzel et al.

[11] Patent Number: 5,343,653
[45] Date of Patent: * Sep. 6, 1994

[54] DEVICE FOR TRANSCUTICULAR APPLICATION OF ACTIVE SUBSTANCE TO PLANTS

[75] Inventors: Hanshelmut Itzel, Gau-Algesheim; Bernd Zierenberg, Bingen; Christo Drandarevski, Ingelheim am Rhein; Wilfried Heupt, Malborn, all of Fed. Rep. of Germany

[73] Assignee: Celaflor GmbH, Ingelheim am Rhein, Fed. Rep. of Germany

[ * ] Notice: The portion of the term of this patent subsequent to Apr. 13, 2010 has been disclaimed.

[21] Appl. No.: 127,458

[22] Filed: Sep. 27, 1993

Related U.S. Application Data

[60] Continuation of Ser. No. 936,006, Aug. 27, 1992, abandoned, which is a division of Ser. No. 844,866, Mar. 2, 1992, Pat. No. 5,201,925, which is a continuation of Ser. No. 727,362, Jul. 9, 1991, abandoned, which is a continuation of Ser. No. 601,604, Oct. 23, 1990, abandoned, which is a continuation of Ser. No. 453,176, Dec. 26, 1989, abandoned, which is a continuation of Ser. No. 74,277, Jul. 16, 1987, abandoned.

[30] Foreign Application Priority Data

Jul. 17, 1986 [DE] Fed. Rep. of Germany ....... 3624074

[51] Int. Cl.$^5$ .............................................. A01B 79/02
[52] U.S. Cl. ........................................... 47/1.5; 47/58
[58] Field of Search .................... 47/1.5, 1.7, 48.5, 55, 47/56, 57.5, 58; 424/448, 449

[56] References Cited

U.S. PATENT DOCUMENTS

| | | | |
|---|---|---|---|
| 1,860,255 | 5/1932 | L'Hommedieu | 47/7 |
| 2,579,403 | 12/1951 | Slomowitz et al. | 604/307 X |
| 2,786,306 | 3/1957 | Eaton et al. | 47/5.5 |
| 3,996,934 | 12/1976 | Zaffaroni | 424/448 X |
| 4,167,832 | 9/1979 | Zetterquist et al. | 47/7 X |
| 4,198,782 | 4/1980 | Kydonieus et al. | 111/130 X |
| 4,291,497 | 9/1981 | Manankov | 47/57.5 X |
| 4,390,519 | 6/1983 | Sawyer | 424/447 |
| 4,402,696 | 9/1983 | Gulko . | |
| 4,470,962 | 9/1984 | Keith et al. | 424/448 X |
| 4,655,768 | 4/1987 | Marecki et al. | 604/307 X |
| 4,663,228 | 5/1987 | Bolton et al. | 604/307 |
| 4,747,845 | 5/1988 | Korol . | |
| 4,797,284 | 1/1989 | Loper et al. . | |

Primary Examiner—Danton D. DeMille
Attorney, Agent, or Firm—James G. Passé

[57] ABSTRACT

A device for the transcuticular administration of active substances to plants, and a method of using the same to treat plants with fungicidal, herbicidal, insecticidal and/or acaricidal substances.

2 Claims, 1 Drawing Sheet

DEVICE FOR TRANSCUTICULAR APPLICATION OF ACTIVE SUBSTANCE TO PLANTS

This is a continuation of application Ser. No. 07/936,006 filed Aug. 27, 1992, now abandoned, which is a divisional application of application Ser. No. 07/844,866 filed Mar. 2, 1992, now U.S. Pat. No. 5,201,925, which in turn a continuation of application Ser. No. 07/727,362 filed Jul. 9, 1991, now abandoned, which is in turn a continuation of application Ser. No. 07/601,401 filed Oct. 23, 1990, now abandoned, which in turn a continuation of application Ser. No. 07/453,176 filed Dec. 26, 1989, now abandoned, which is in turn a continuation of application Ser. No. 07/074,277 filed Jul. 16, 1987, abandoned.

FIELD OF INVENTION

This invention relates to a device for transcuticular application of metered quantities of an active substance to plants, and to processes for the preparation of such a device.

BACKGROUND OF THE INVENTION

In the field of plant protection, it is known to apply active substances to the plants by spraying or dusting compositions which contain the active substance onto the plants. The active substance acts either by direct contact or systemically, that is, it is absorbed by the plant through the cuticles of the leaves.

The methods heretofore used have some serious disadvantages. On the one hand, there is a clear imbalance between the quantity of active substance required on or in the plant to achieve a positive effect and the quantity of active substance actually applied by spraying or dusting.

On the other hand, the application of plant-protecting substances by spraying or dusting requires certain precautions to prevent damage to the health of anyone present, which cannot always be adhered to particularly in the case of houseplants and horticulture. The storage of large quantities of concentrated active substances constitutes an additional hazard. Moreover, the user, particularly at a domestic or horticultural level, generally finds it impossible to meter the active substance accurately onto the plant. This does not mean the preparation of a solution from a concentrate containing the active substance, but the actual quantity of solution which is sprayed onto the plant. In most cases too much or too little solution is sprayed on. Indoor spraying has the further disadvantage that the immediate area surrounding the plant will also be sprayed with active substance, and consequently the plants should ideally be treated in the open. Any unused left-overs of solution which have evaporated to a crust may cause problems if they cannot be disposed of properly.

A further problem when spraying or dusting is the problem of drifting. In many cases it is undesirable that neighboring plants should come into contact with the active substance. This is the case, for example, if vegetables or fruits ready for harvesting are in the vicinity. It is particularly undesirable for drifting to occur when using systemically acting herbicides, for instance those for combating quack grass.

A further disadvantage of previous methods of application is that after the plant protecting substances have been applied it is no longer readily possible to tell which active substance has been used to treat the plant.

OBJECTS OF THE INVENTION

It is an object of this invention to provide a device which improves the ratio of active substance required to active substance applied in the field of plant protection.

A further object is to provide a device which will increase safety when dealing with active substances in the field of plant protection.

Other objects and advantages of the invention will become apparent as the description thereof proceeds.

DESCRIPTION OF THE INVENTION

The above objects are achieved according to the invention by means of a device for the transcuticular application of systemic active substances to plants in the form of an active substance carrier which stores the active substance, one surface of the active substance carrier being constructed as a layer for coming into contact with the plant surface, through which the active substance is released onto the plant.

According to the invention, the device is brought into close contact with the plant so that the active substance passes through the cuticle of the leaf or stalk into the plant and is there distributed throughout the plant by the plant metabolism.

In its simplest embodiment, the device according to the invention consists of a carrier which stores the active substance, as shown schematically in FIG. 1 of the attached drawings.

Suitable carrier materials are those which are capable of storing the active substance in dissolved, suspended or solid form, such as paper, textile fibers, inorganic porous materials such as silicates or carbonates, optionally mixed with binders, or poisoners. Paper and polymers are the preferred carrier materials.

Furthermore, the active substance carrier comprises means for attachment to the plant. These may be mechanical fasteners, for instance in the form of clips or bandages, or adhesive means, the adhesive fastening means being preferred because of the ease of application. It is important that intimate contact is established between the part of the plant and the device so that the active substance passes into the plant.

In one particular embodiment, the underside of the carrier may comprise microfine fibers which penetrate into the outer layer of cells and thus improve the uptake of active substance by the plant.

In another embodiment, the underside of the carrier, the side which will be in contact with the plant, is coated with the active substance in microcrystalline form.

In another embodiment the upper side, that is, the side which will face away from the plant, of the active substance carrier is impregnated to make it water repellent, which ensures that highly water-soluble active substances cannot be washed out. The impregnation may be effected, for example, by spraying the carrier with suitable solutions known to those skilled in the art.

In a particular embodiment, the device according to the invention consists of a carrier with a self-stick polymer containing the active substance. Polymers of suitable composition and glass temperature for this purpose are known to those skilled in the art. To improve the handling of such a carrier it is advantageous if the upper side of the carrier is coated with a non-stick material.

The embodiment of the device according to the invention is of laminate-like construction.

Figure 2:
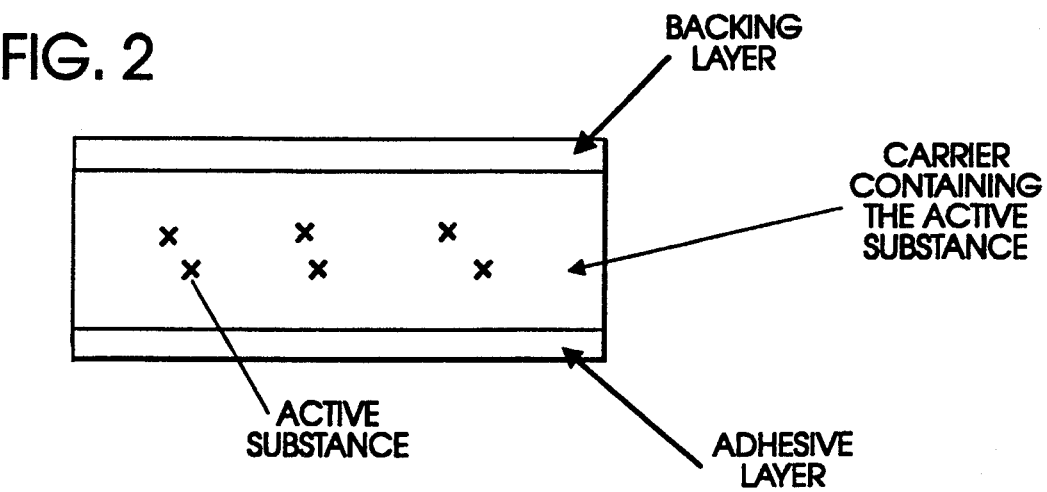

As shown schematically in FIG. 2 of the attached drawings, the laminated device consists of a backing layer, a reservoir of active substance consisting of one or more layers, an adhesive layer and a removable protective layer.

The backing layer, optionally impermeable to the active substance, closes off the structure of the laminates on the side which will face away from the plant. Suitable materials for forming the backing layer are polymers such as PVC, thin metal films, for instance of aluminum, optionally coated with a thin polymer film. If desired, the backing layer may be colored so that the device is clearly visible on the plant. In another embodiment, the backing layer may be constructed, for instance by means of a metal insert or textile insert, so that it acts as a support layer for stabilizing the laminate.

In a particular embodiment, the backing layer has a larger surface area than the active substance reservoir arranged next to it and is coated on its underside with an adhesive material. In this way it simultaneously serves to fix the reservoir of active substance to the plant. Obviously, in this embodiment the separate adhesive layer shown in FIG. 2 is not required.

Adjoining the backing layer is the reservoir of active substance which may consist of one or more layers, although not all the layers need contain active substance.

A multi-layer reservoir with layers of different active substances permits storage of combinations of active substances. The layers may contain agents which give slow release of the active substance. In particular, membrane-like layers are suitable for controlling the release of active substance.

Materials which are suitable for forming the reservoir containing the active substance are those which will store the active substance in solid, liquid or dissolved form and release it to the plant under controlled conditions.

The active substance may be embedded in the form of microcapsules in a polisher or may be present dispersed in a polymer matrix. It is also possible for the reservoir to form a cavity in which the active substance is contained, for example in liquid forth.

Suitable polymers for forming the active substance carrier or the reservoir layer include, for example, polyvinyl alcohol, polyvinyl acetate, plasticized polyvinyl chloride, plasticized polyamide, gelatin, waxes, polymers of monoesters of olefinic acids such as acrylic acid, methacrylic acid, polyhydroxyalkylacrylates or silicone rubbers.

Emulsion polymers such as PVC, polystyrene, polyvinyl acetates, polybutadiene, polyacrylonitrile, polyvinyl esters, polyvinyl ethers and copolymers thereof are particularly preferred.

Emulsion-polymerized copolymers of methyl and/or ethyl esters of acrylic and methacrylic acid are especially preferred.

Fillers such as silica, for example, may be added to the polymers.

Adjoining the active substance reservoir is an adhesive layer. Self-stick polymers are well known to those skilled in the art. By a suitable choice of polymers the composition of the adhesive layer may be chosen so that it controls the rate of release of the active substance from the reservoir layer. Besides adhesive layers extending over the entire surface it is also possible to have adhesive surfaces using rings or dots of adhesive. Adhesive surfaces extending over he entire area must, in any case, be permeable to the active substance. This adhesive layer may be omitted if the active substance reservoir consists of a self-stick polymer or the enlarged backing layer also has, on its underside, an adhesive layer which extends beyond the layer of active substance.

For protection, the reservoir of active substance has a removable protective film adjoining the adhesive layer; alternatively, the entire reservoir of active substance may be sealed into a film which can be torn open. This arrangement is particularly recommended if the active substances involved are highly volatile.

In another embodiment, the device according to the invention is in the form of a sticker or label. The outside (back) of the device is constructed so that it can be written on, for example, it is made of a paper-based material or a polymer film which can be written on. Important information such as the date of application to the plant, etc., can be written on the back.

It is also possible to print thereon important information such as the name of the active substance, storage dates or the duration of activity of the device from the date of application, during the actual manufacture of the device. Other markings, such as color codes or graphic symbols, may also readily be printed or stamped on.

These features provide, for the first time, a plant-protecting device which will enable anyone to tell which active substance has been used on the plant, even after the substance has been applied, without any additional tests being required.

The device according to the present invention is suitable for transcuticular application of metered quantities of active substance to plants of all genera, particularly house and garden plants.

For this purpose, it is applied to the leaves or stems of the plants, so that intimate contact is maintained between the plant and the device and the active substance passes out of the reservoir and penetrates into the plant.

The transcuticular application of fungicidal and/or insecticidal active substances may be used to combat or ward off pests. The device of the instant invention is particularly suitable for herbicidal treatment of individual plants. Suitable active substances in terms of the invention are those compounds which have a fungicidal, herbicidal, insecticidal and/or acaricidal activity on the basis of their systemic effect.

The following tables list the preferred active substances which may be applied, either singly or in combination, by means of the device according to the present invention.

| SYSTEMIC active substances |
|---|
| 1. with insecticidal, acaricidal and aphicidal activity |
| Active substance |
| Acephate |
| Aldicarb |
| Aldocycarb |
| Demeton |
| Demeton-S-m |
| Dicrotophos |
| Dimefox |
| Dimethoate |
| Formothion |
| Methamidophos |
| Methomyl |
| Mevinphos |
| Monocrotophos |
| Morphothion |
| Omethoate |
| Oxamyl |

| SYSTEMIC active substances | | |
|---|---|---|
| Oxydemetron-m. | | |
| Phosphamidon | | |
| Prothoate | | |
| Thiometon | | |
| Vamidothion | | |
| 2. with aphicidal activity | | |
| Aphidan | | |
| Butocarboxim | | |
| Butoxycarboxim | | |
| Heptenophos | | |
| 3. Systemic fungicides | | |
| Benomyl | Dodemorph | Nuarimol |
| Benodanil | Etaconazol | Oxycarboxin |
| Kitazin | Fenarimol | Prochloraz |
| Bitertanol | Fenpropimorph | Propiconazol |
| Carbendazim | Fosetyl | Triadimefon |
| Carboxin | Furalaxyl | Triadimenol |
| Cyprofuram | Imazalil | Tridemorph |
| Dichlobutrazol | Metalaxyl | Triforine |
| 4. Herbicides | | |
| Acifluorfen | Chlortoluron | Gibberellic acid |
| Alachlor | 2,4-D | Glufosinate |
| Alloxydim | Dalaphon | Glyphosate |
| Bentazon | 2,4-DB | Glyphosine |
| Bromoxynil | Dicamba | Ioxynil |
| Chlorfluorenol | Dichlorprop | MCPA |
| Chloridazon | Dichlofop | Mecoprop |
| Chlormequat | Diquat | Paraquat |
| Chloroacetic acid | Fluazifop | Pyridate |
| Chlorsulfuron | Flurenol | Sulfometuron |

The device according to the invention may contain the active substance in concentrations of between $10^{-6}$ and 200 mg, preferably 0.01–100 mg per device. The exact dosage depends on various parameters such as the nature of the polymer, the nature of the active substance carrier, the intended period of application, the thickness of the reservoir layer, and can be determined by simple experiments. Using the precisely predetermined quantity of active substance in the device, it is possible even for non-experts to apply the required quantity of active substance to achieve the desired effect without over- or under-dosing. This is not always guaranteed by simply spraying or dusting.

The size of the area of contact of the device is not critical but should be such that it does not extend beyond the parts of the plant, and normally it ranges from 1 to 20 $cm^2$. The thickness of the device depends on the materials used, the layer structure, the quantity of active substance per unit area and the quantity of active substance which is intended to be delivered per unit time. It is generally between 5 microns and 200 microns, preferably up to 100 microns, and can easily be determined by experiment.

Numerous advantages arise from using the device of the present invention for the transcuticular application of systemic active substances to combat pests.

The active substances are fixed on the plant over a closely defined area in an outwardly "sealed" reservoir and not, as would be unavoidable when spraying or dusting, uniformly distributed through the mediate vicinity of the plant. Accidental contact with the active substance is virtually eliminated. No protective precautions, such as breathing masks or the like, are required when applying the substances. At the end of the treatment any unused residues of active substance can be disposed of relatively easily by removing the reservoir of active substance and discarding it in the usual way. Useful insects, such as bees, are not endangered either during application of the active substance or during the period of treatment.

The active substance can be protected from external influences, such as UV radiation or washing away by rain, by being contained in the active substance reservoir. Consequently, preventive long-term treatment of the plants is substantially less problematic than with conventional methods. It is also easier to use sensitive active substances.

The quantity of active substance actually applied is drastically reduced compared with that used for dusting or spraying. Accidental contact with the active substance and even direct contact with the active substance layer is not dangerous, compared with conventional preparations, because the active substance is relatively firmly fixed in the reservoir.

The device of the present invention may be produced, for example, by the following methods. The active substance is dissolved or suspended, together with the polymer and any additives which may be used, in a volatile organic solvent, then poured out to produce a film of predetermined thickness and dried. The reservoir of active substance thus obtained can subsequently be provided with a backing layer, an adhesive layer and a protective coating and packaged.

If the carrier material consists of an absorbent material such as paper, the active substance reservoir can be produced by simply saturating the absorbent material with a solution of the active substance; this may be done, for example, by immersion or spraying.

The active substance may also be printed onto the carrier material using known printing methods, for instance on a polymer or preferably on paper.

A carrier such as paper charged with active substance may be provided with a backing layer which is sticky on the underside. After a removable protective film has been applied, the resulting laminate is cut to the required size.

In another embodiment, the active substance carrier is fixed to the plant by means of an adhesive tape cover.

Active substance reservoirs having a fine crystalline layer of active substance on their underside may be prepared by simply applying the fine crystalline active substance to a sticky carrier material.

TRIALS

A) Preparation of the Device According to the Invention

Composition of the active substance carrier layer

EXAMPLE 1

| |
|---|
| 14.8 g Eudragit ® E 30 D (polymer) |
| 5.2 g Dimethoate |
| 20.0 g Solid matter |
| 80.0 g Acetone |
| 100 g Solution |

The polymer is dissolved, together with the active substance, in acetone and the solution is poured out to form a film on a carrier foil (12 microns). After drying, the total thickness is about 100 microns.

EXAMPLE 2

Composition

| |
|---|
| 13.8 g Eudragit ® 30 D |

-continued

| | |
|---|---|
| 1.0 g | Isopropyl myristate |
| 5.2 g | Dimethoate |
| 20.0 g | Solid matter |
| 80.0 g | Acetone |
| 100.0 g | Solution |

The method used is as described in Example 1; in this case the adhesive layer is self-sticking.

B) Biological tests

1. Material and methods 1.1 Preparations

The devices (circular, about 5 cm²) are characterized as follows:

| Charge | Dimethoate Concentration mg/cm² | Thickness of carrier foil microns | Thickness of adhesive layer microns |
|---|---|---|---|
| 1 | approx. 2.5 | 12 | approx. 80 |
| 2 | approx. 0.5 | 12 | approx. 40 |
| 3 | approx. 0.5 | 12 | approx. 80 |

1.2. Test method

The device is applied by simply pressing it: onto the top of the leaf in the lowest leaf area; onto the underside of the leaf in the lowest leaf area; onto the stalk or petiole.

For the first test batch using Vicia plants a single reservoir was applied to each plant or leaf. In the second test batch on ornamental plants, 1–4 reservoirs were applied per plant or petiole.

Figure 3:
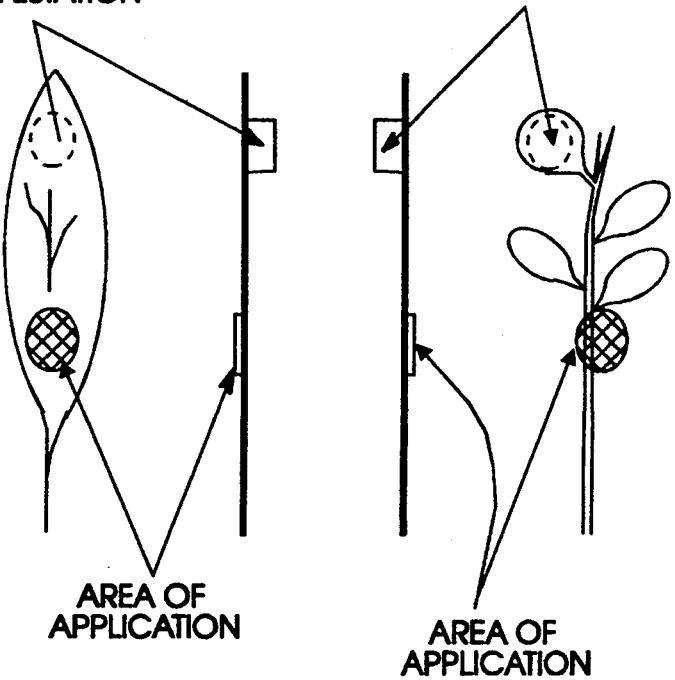

Infestation with *Aphis fabae* was then carried out after application by means of small dishes containing about 50 aphids, always on the uppermost leaf area, and accordingly on the other, untreated side of the leaf. Where the active substance had been applied to the stem, infestation was carried out on the top layer of leaves (see FIG. 3 of the attached drawings).

The results were evaluated by counting the number of dead and living aphids (given as % mortality or activity) for Vicia after 1, 2 and in some cases 4 days. For the second test on ornamental plants, the results were evaluated 7 days after application.

2. Results

The test results from the first test on Vicia plants are shown in Table 1. These results show that dimethoate exhibits a translaminar and a systemic activity when applied by this method. The type of activity depends on the dosage.

We also found that the highest activity rates are achieved when the active substances are applied to the stem. The plant tolerance depends on the dosage and site of application, the latter being the critical factor. For example, at points where the dimethoate is rapidly transported away, namely on the stem, no phytotoxicity is observed even at the higher dosage.

TABLE 1

Activity (% A.) and tolerance (% Phyt.) of the device of the instance invention used against Aphis fabae after application to various sites and as a function of time

| | | Evaluation after application/infestation | | | | | |
|---|---|---|---|---|---|---|---|
| | Site of appli- | 1st day | | 2nd day | | 4th day | |
| Charge | cation | % A. | % Phyt. | % A. | % Phyt. | % A. | % Phyt. |
| 1 | Stem | 82 | 0 | 100 | 0 | 100 | 0 |
| 2 | | 45 | 0 | 76 | 0 | — | — |
| 3 | | 35 | 0 | 54 | 0 | — | — |
| 1 | Top of | 37 | 7 | 25 | 20 | 65 | 15 |
| 2 | leaf | 5 | 0 | 11 | 0 | — | — |
| 3 | | 7 | 0 | 10 | 0 | — | — |
| 1 | Under- | 20 | 3 | 33 | 15 | 39 | 25 |
| 2 | side | 6 | 0 | 7 | 0 | — | — |
| 3 | of leaf | 4 | 0 | 8 | 6 | — | — |

Tests of Herbicidal Activity 1 mg of Glyphosate in a device according to the invention in the form of a paper-based sticker, 3 cm².

Test Object

Quack grass in cotoneaster crops

Test method

One reservoir is attached to a leaf of each quack grass plant. After 3 days the state of the plants is evaluated.

| | % quack grass killed |
|---|---|
| treated | 100% |
| untreated | 0% |

There were no signs of phytotoxicity in the cotoneasters.

Effectiveness Against Spider Mites

Spider mites on potted hibiscus

Test Method

Sets of 2 hibiscus plants are placed side by side under different spatial conditions. Natural attack by spider mites is awaited. Then each plant is treated with 1 reservoir of 0.5 cm in diameter containing 10 mg of dimethoate. After 1 week and after 2 weeks the activity is evaluated (activity %)

| | Application to stem | Application to underside of leaf | Application to top of leaf |
|---|---|---|---|
| untreated | — | 0% (after 1½ weeks the plants had died off) | |
| treated | | | |
| 1st week | 80 | 70 | 75 |
| 2nd week | 100 | 90 | 92 |

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A device for transcuticular administration to a plant of a substance systemically active in the plant, the device being in the form of a laminate including a systemically active substance to be released to the plant in metered quantities, said laminate comprising in order:

(1) a backing layer impervious to the active substance, (2) an internal active substance reservoir layer formed of a carrier matrix in the form of a polymeric or absorbent material layer having incorporated therein said active substance, and (3) an outer adhesive layer adherable to the plant and permeable to the active substance, said laminate being adhered to said plant through contact with said adhesive layer, and releasing said active substance in metered quantities from said reservoir layer through said adhesive layer to said plant.

2. A device for transcuticular administration to a plant of a substance systemically active in the plant which comprises a device in the form of a laminate including a systemically active substance to be released to the plant in metered quantities, said laminate comprising in order:

(1) a backing layer impervious to the active substance, (2) an adhesive layer coextensive with said backing layer and (3) an external active substance reservoir layer formed of a carrier matrix in the form of a polymeric or absorbent material layer having incorporated therein said active substance, and wherein said reservoir layer is coextensive with only a portion of said adhesive layer which device is adherable to said plant through the portion of said adhesive layer not coextensive with said reservoir layer to bring said reservoir layer in contact with said plant, which will release said active substance in metered quantities through said reservoir layer directly to said plant.

* * * * *